United States Patent
Seo et al.

(10) Patent No.: US 8,431,166 B2
(45) Date of Patent: Apr. 30, 2013

(54) **COMPOSITION COMPRISING THE EXTRACT OF *ANEMARRHENA ASPHODELOIDES* BUNGE OR THE COMPOUNDS ISOLATED FROM THE SAME FOR PREVENTING AND TREATING LIPID METABOLISM DISORDER**

(75) Inventors: Eun Kyoung Seo, Seoul (KR); Eun Sook Hwang, Seoul (KR); Ui Joung Youn, Daejeon (KR); Joo Won Nam, Seoul (KR)

(73) Assignee: EWHA University-Industry Collaboration Foundation, Seoul (KR)

( * ) Notice: Subject to any disclaimer, the term of this patent is extended or adjusted under 35 U.S.C. 154(b) by 0 days.

(21) Appl. No.: 13/264,451

(22) PCT Filed: Dec. 8, 2009

(86) PCT No.: PCT/KR2009/007327
§ 371 (c)(1),
(2), (4) Date: Dec. 7, 2011

(87) PCT Pub. No.: WO2010/120029
PCT Pub. Date: Oct. 21, 2010

(65) Prior Publication Data
US 2012/0070515 A1   Mar. 22, 2012

(30) Foreign Application Priority Data

Apr. 16, 2009 (KR) .................. 10-2009-0033011
May 7, 2009 (KR) .................. 10-2009-0039689

(51) Int. Cl.
*A01N 65/00* (2009.01)
(52) U.S. Cl.
USPC .................................................. 424/725

(58) Field of Classification Search .................. None
See application file for complete search history.

(56) References Cited

FOREIGN PATENT DOCUMENTS
KR    10-0856335 B1    6/2007

OTHER PUBLICATIONS

Bae, Green, et al, "Identification of Nasoi and Structurally Related Compounds as the Active Principles from *Anemarrhena asphodeioides* against Respiratory Syncytiai Virus (RSV)," Chemistry & Biodiversity, 2007, 4:2231-2235.
Guo, Jian, et al., "Biotransformation of the Chemopreventive Agent 2',4',4-Trihydroxychalcone (Isoliquiritigenin) by UDP-Glucuronosyltransferases," Drug Metabolism and Disposition, 2008, 36/10:2104-2112.
Islam, M. Nurul, et al. "Simultaneous Determination of Bioactive Xanthone Glycosides and Norlignans from Ethanolic Extract of *Anamarrhena asphodeloides* by Liquid Chromatography," Journal of AOAC International, 2008, 91/6:1271-.
Song, Myoung-Chong, et al., "Antioxidant and Antiatherogenic Activity of cis-Hiriokiresinol from Trapa pseudoincisa," Archive of Pharmacal Research, 2007, 30/11:1392-1397.
Zhang, Hong-Jie, et al., "Bioactive Constituents from Asparagus cochinchinensis," J. Nat. Prod., 2004, 67:194-200.
International Search Report and Written Opinion for PCT/KR2009/007327 dated Aug. 13, 2010.

*Primary Examiner* — Michael Meller
(74) *Attorney, Agent, or Firm* — Chainey P. Singleton; Daniel J. Chalker; Chalker Flores, LLP

(57) ABSTRACT

The present invention relates to a composition comprising an extract of *Anemarrhena asphodeloides* Bunge or the compounds isolated from the same, as an active ingredient. In particular, the extract and compounds have the excellent inhibitory effects on adipocyte differentiation, and thus can be used in a pharmaceutical composition and functional food for the prevention and treatment of lipid metabolism disorders.

3 Claims, 1 Drawing Sheet

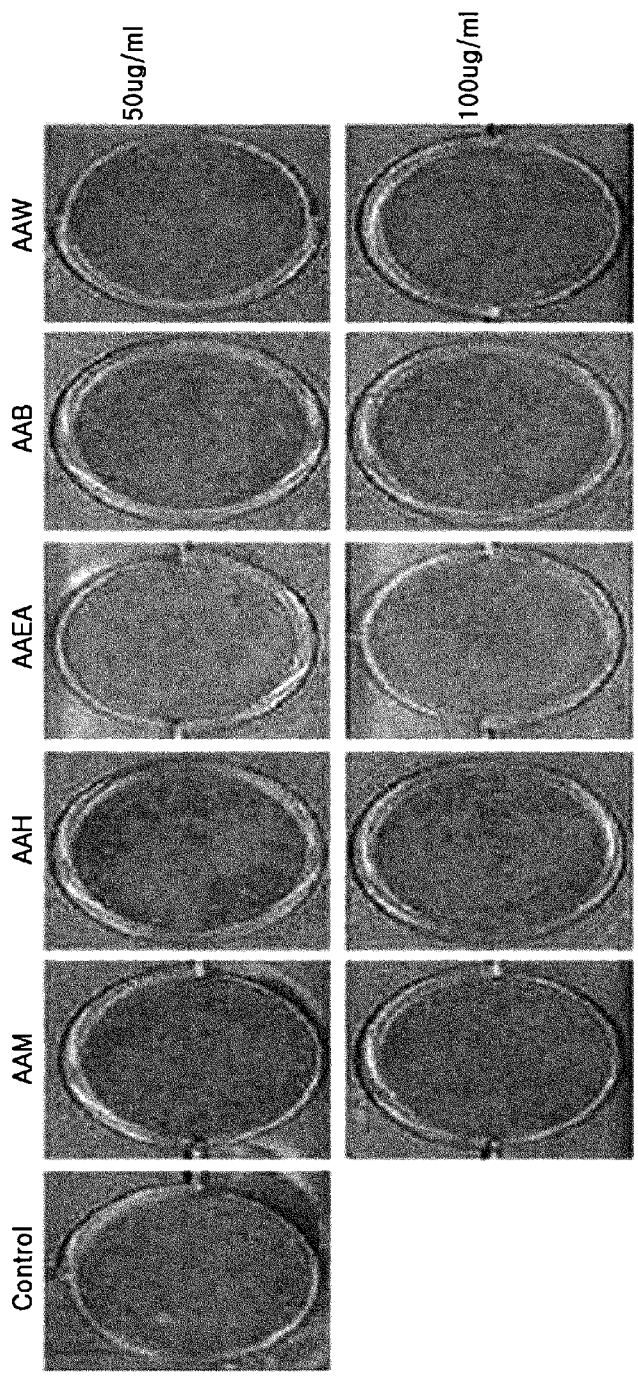

COMPOSITION COMPRISING THE EXTRACT OF *ANEMARRHENA ASPHODELOIDES* BUNGE OR THE COMPOUNDS ISOLATED FROM THE SAME FOR PREVENTING AND TREATING LIPID METABOLISM DISORDER

TECHNICAL FIELD

The present invention relates to a composition for the prevention and treatment of lipid metabolism disorders, comprising the extract of *Anemarrhena asphodeloides* Bunge or the compounds isolated from the same having an inhibitory effect on adipocyte differentiation as an active ingredient.

BACKGROUND ART

Obesity is the most common nutritional disorder in industrialized countries. US statistics show that more than one third of U.S. adults and 20% of U.S. children are obese, and more than 70% of patients with type II diabetes are obese. Obesity is also a major risk factor for the development of hypertension, hyperlipidemia and some types of cancer. It has been known that obesity is particularly prevalent in patients with carbohydrate metabolism disorders and non-insulin-dependent diabetes mellitus, and weight gain exacerbates the diabetic condition, but the causal nature between diabetes and obesity remains unclear. Not all patients with extremely severe obesity will have diabetes, and obesity alone is not sufficient to cause non-insulin-dependent diabetes mellitus, and either genetic or environmental factors are recognized to be involved in its onset. However, the incidence of non-insulin-dependent diabetes mellitus is much higher in obese people, and also closely related to the degree and duration of obesity. Thus, obesity is a major risk factor for non-insulin-dependent diabetes mellitus.

Meanwhile, body fat distribution as well as degree of obesity has been recently reported to be closely related to obesity-related disorders. Abdominal obesity, in particular, is a growing public health problem.

Patients with non-insulin-dependent diabetes mellitus commonly have obesity or a previous history of obesity. It was reported that 60~90% of Western people with non-insulin-dependent diabetes mellitus are obese and about 70% of Korean patients with non-insulin-dependent diabetes mellitus have a previous history of obesity (Joong-Yeol Park et al., Body Weight Changes of Non-Insulin Dependent Diabetic Patients in Korea, Diabetes, 17, pp. 51-57, 1993).

Many prospective studies revealed that obesity precedes the development of impaired glucose tolerance and non-insulin-dependent diabetes mellitus (Carey V J. et al., Body fat distribution and risk of non-insulin-dependent diabetes mellitus in women, The nurses' health study, Am J Epidemiol, 145, pp. 614-619, 1997). The Framingham study demonstrated that impaired glucose tolerance is frequently observed in obese people, and most studies showed that obese people with impaired glucose tolerance are at a high risk for developing non-insulin-dependent diabetes mellitus.

A mechanism for the development of diabetes from obesity has not been clarified yet, but increased insulin resistance is regarded as a key factor. Felber et al., on the basis of the epidemiological evidence, divided obese people into four groups (normal glucose tolerance, impaired glucose tolerance, hyperinsulinemic diabetes, and hypoinsulinemic diabetes groups), depending on glucose and insulin responses after an oral glucose tolerance test, and they suggested that this process is involved in the development of diabetes from obesity (Golay A. et al., Obesity and NIDDMP, the retrograde regulation concept, *Diabetes Rev,* 5, pp. 69-82, 1997).

Carbohydrate metabolism in obesity shows insulin resistance, which is defined as normal glucose level and elevated insulin level in response to the oral glucose tolerance test. Insulin resistance is a central pathological defect found in obesity patients and obese patients with non-insulin-dependent diabetes mellitus, and is observed in the early stages of obesity. There have been many hypotheses on the mechanism concerning the reduced insulin action in obesity, but it is not clarified yet. That is, functional reduction of insulin receptors involved in insulin action, glucose receptors, and enzymes involved in glucose synthesis and glucose oxidation is observed in the obese, which is understood as a secondary phenomenon due to obesity (Golay A. et al., Obesity and NIDDMP, the retrograde regulation concept, *Diabetes Rev,* 5, pp. 69-82, 1997).

Some circumstantial evidence suggests that adipocyte plays a central role in the development of the insulin resistance. That is, several adipocyte-secreted factors or metabolic messengers are considered to impair insulin action in the muscle and liver. A first, widely recognized factor is extracellular free fatty acids generated by the hydrolysis of storage triglyceride in the adipose tissue. In addition, TNF-α and leptin secreted by adipose tissue are recently suggested to cause insulin resistance in obesity (Hotamisligil G S. et al., Tumor necrosis factor a, a key component of the obesity-diabetes link, *Diabetes,* 43, pp. 1271-1278, 1994).

Energy metabolism in obesity tends to increase both degradation and synthesis of lipids. Obesity, in particular, abdominal obesity, is characterized by an increase in lipid degradation and free fatty acid availability. Reportedly, there is a strong correlation between body fat mass and fat oxidation, suggesting that the increased blood free fatty acid level and lipid oxidation are attributed to the increase in fat mass. Increased lipid oxidation is observed even in the early stages of obesity, and also on an empty stomach or after a glucose load.

In Korea, the number of obese people is dramatically increasing because of the improved living standard and Westernized eating habits. Obesity causes or worsens many diseases including hypertension, arteriosclerosis, fatty liver, and diabetes. Therefore, prevention of obesity is important, and when obesity occurs, it is necessary to activate the body metabolism through reduction of body fat and improvement of lipid metabolism for health promotion and disease prevention.

*Anemarrhena asphodeloides* Bunge (called Ji-mo in Korea), is a perennial herb belonging to the family Liliaceae, and the dried root-like stem of *Anemarrhena asphodeloides* Bunge is used in traditional medicine. *Anemarrhena asphodeloides* Bunge is native to northern China, and widely grows in Korea (Hwang Hae and Pyong-nam Province), China, Mongolia and the region. Since the rhizome looks like a bug, it is called Ji-mo in Korea, a play on words in the Korean language. It has a distinctive odor, and is slightly bitter and sweet in taste, and viscous when chewed. It has diuretic, antipyretic, and antitussive effects.

*Anemarrhena asphodeloides* Bunge was known to contain about 6% steroid saponin, timosaponin A-I, A-II, A-III, and A-IV (water-insoluble part of methyl alcohol X), timosaponin B-I and B-II (water-soluble part), sarsasapogenin, markogenin, and neogitogenin as saponin, xanthone; mangiferin, isomangiferin, and 200 μg/g of nicotinic acid as vitamin (Park Jong-Hee, the encyclopedia of Chinese crude drugs (Vol. 2), Sinil Sangsa, pp. 746-748, 2002), but there is no previous mention that an extract of *Anemarrhena asphodeloides* Bunge or compounds isolated from the same improve lipid metabolism.

DISCLOSURE OF INVENTION

Technical Problem

Accordingly, the present inventors examined the inhibitory effect of an extract of *Anemarrhena asphodeloides* Bunge and compounds isolated from *Anemarrhena asphodeloides* Bunge on adipocyte differentiation. They found that the extract of *Anemarrhena asphodeloides* Bunge and the compounds have excellent inhibitory effect on adipocyte differentiation, and thus are very useful for the prevention and treatment of lipid metabolism disorders, thereby completing the present invention.

Solution to Problem

The present invention relates to a composition comprising an extract of *Anemarrhena asphodeloides* Bunge or the compounds isolated from the same, as an active ingredient. In particular, the extract and compounds have the excellent inhibitory effects on adipocyte differentiation, and thus can be used in a pharmaceutical composition and functional food for the prevention and treatment of lipid metabolism disorders.

Advantageous Effects of Invention

As described above, the extract of *Anemarrhena asphodeloides* Bunge and the compounds isolated from *Anemarrhena asphodeloides* Bunge of the present invention have excellent inhibitory effect on adipocyte differentiation, and thus can be used as a pharmaceutical composition for the prevention and treatment of lipid metabolism disorders.

BRIEF DESCRIPTION OF DRAWINGS

FIG. 1 shows inhibitory effects on adipocyte differentiation of the extracts of *Anemarrhena asphodeloides* Bunge.

BEST MODE FOR CARRYING OUT THE INVENTION

In order to achieve the above objects, the present invention provides a novel compound of (E)-5,7-dihydroxy-3-(4'-hydroxybenzylidene)-6-methylchroman-4-one, 7-hydroxy-3-(4-hydroxybenzyl)coumarin, or 1,3-bis(4-hydroxyphenyl)prop-2-yn-1-one represented by the following Formulas (a), (b), or (c), which is isolated from *Anemarrhena asphodeloides* Bunge, or a pharmaceutically acceptable salt thereof;

[Formula 1]

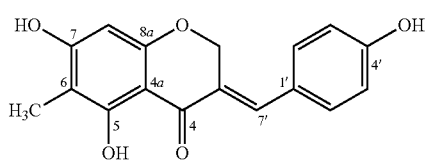

The compound of Formula (a), as used herein, is designated as (E)-4'-demethyl-6-methyleucomin ((E)-5,7-dihydroxy-3-(4'-hydroxybenzylidene)-6-methylchroman-4-one).

[Formula 2]

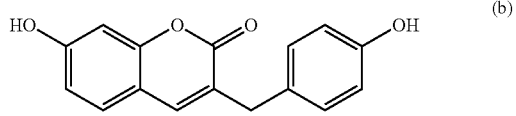

The compound of Formula (b), as used herein, is designated as anemarcoumarin A (7-hydroxy-3-(4-hydroxybenzyl)coumarin).

[Formula 3]

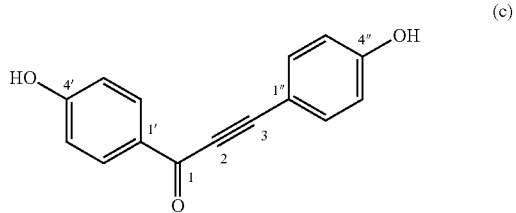

The compound of Formula (c), as used herein, is designated as anemarchalconyn (1,3-bis(4-hydroxyphenyl)prop-2-yn-1-one).

The compound represented by Formulas (a), (b) or (c) may be prepared in the form of a pharmaceutically acceptable salt according to the conventional method in the related art.

As the pharmaceutically acceptable salt, acid addition salts produced with pharmaceutically acceptable free acids are preferred. The acid addition salts may be prepared through conventional methods. For example, acid addition salt may be prepared by dissolving the compound in an excessive amount of an acid aqueous solution, and precipitating the salt in a water-miscible organic solvent, such as methanol, ethanol, acetone or acetonitrile. Acid addition salt may be also prepared by heating a mixture including the same amount of the compound and an acid in water or alcohol (e.g., glycol monomethylether), and then drying the mixture or performing suction filtration onto the educed salt.

As the free acids, organic acids and inorganic acids may be used. Examples of the inorganic acids may include hydrochloric acid, phosphoric acid, sulfuric acid, nitric acid, and tartaric acid, and examples of the organic acids may include methanesulfonic acid, p-toluenesulfonic acid, acetic acid, trifluoroacetic acid, citric acid, maleic acid, succinic acid, oxalic acid, benzoic acid, tartaric acid, fumaric acid, manderic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, and hydroiodic acid.

Further, the pharmaceutically acceptable metal salt form may be prepared by using a base. The alkali metal or alkali-earth metal salt thereof may be prepared by the conventional method; for example, after dissolving the compound in the excess amount of alkali metal hydroxide or alkali-earth metal hydroxide solution, the insoluble salts are filtered and remaining filtrate is subjected to evaporation and drying to obtain the metal salt thereof. As a metal salt, sodium, potassium or calcium salt is pharmaceutically suitable. In addition, the corresponding silver salt may be prepared by reacting alkali metal salt or alkali-earth metal salt with suitable silver salt (e.g., silver nitrate).

The pharmaceutically acceptable salt of the compound of Formulas (a), (b) or (c) comprise all the acidic or basic salts which may be present at the compound of Formulas (a), (b) or (c), if it is not indicated specifically herein. For example, the pharmaceutically acceptable salt comprises the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonate(mesylate) salt and p-toluenesulfonate (tosylate) salt etc, which may be prepared by the conventional method well known in the art.

The present invention provides a pharmaceutical composition for the prevention and treatment of lipid metabolism disorders, comprising an extract of *Anemarrhena asphodeloides* Bunge, as an active ingredient.

The extract comprises crude extract, polar solvent soluble extract, or nonpolar solvent soluble extract of *Anemarrhena asphodeloides* Bunge.

The crude extract is extracted using a solvent selected from the group consisting of water, C1 to C4 lower alcohol, and the mixtures thereof, preferably water, methanol, ethanol and the mixtures thereof, more preferably methanol or ethanol of 60~100%.

The polar solvent soluble extract is extracted using a solvent selected from the group consisting of water, methanol, ethanol, butanol and the mixtures thereof, preferably water and butanol.

The nonpolar solvent soluble extract is extracted using an eluting solvent selected from the group consisting of hexane, chloroform, dichloromethane, methylenechloride, ethylacetate, glycerine and buthyleneglycol, preferably hexane and ethylacetate.

The present invention provides a pharmaceutical composition for the prevention and treatment of lipid metabolism disorders, comprising the novel compound represented by Formulas (a), (b) or (c), or a pharmaceutically acceptable salt thereof, which is isolated from *Anemarrhena asphodeloides* Bunge, as an active ingredient.

The present invention provides a pharmaceutical composition for the prevention and treatment of lipid metabolism disorders, comprising a compound selected from 4'-O-methylnyasol, Nyasol, Broussonin A, 1,3-bis-di-p-hydroxyphenyl-4-penten-1-one, 2',4',4-trihydroxychalcone, 7,4'-dihydroxyhomoisoflavane, 2'-O-methylisoliquiritigenin, 2,4',6-trihydroxy-4-methoxybenzophenone, 4',7-dihydroxy-5-methoxyflavanone, 2'-O-methylphloretin and 4,4'-dihydroxychalcon represented by the following Formulas (d) to (n), which are isolated from *Anemarrhena asphodeloides* Bunge, as an active ingredient.

Further, the present invention provides a functional food for the prevention and improvement of lipid metabolism disorders, comprising the extract of *Anemarrhena asphodeloides* Bunge, as an active ingredient.

Further, the present invention provides a functional food for the prevention and improvement of lipid metabolism disorders, comprising the novel compound represented by Formulas (a), (b) or (c), or the pharmaceutically acceptable salt thereof, which is isolated from *Anemarrhena asphodeloides* Bunge, as an active ingredient.

The present invention provides a functional food for the prevention and improvement of lipid metabolism disorders, comprising a compound selected from 4'-O-methylnyasol, Nyasol, Broussonin A, 1,3-bis-di-p-hydroxyphenyl-4-penten-1-one, 2',4',4-trihydroxychalcone, 7,4'-dihydroxyhomoisoflavane, 2'-O-methylisoliquiritigenin, 2,4',6-trihydroxy-4-methoxybenzophenone, 4',7-dihydroxy-5-methoxyflavanone, 2'-O-methylphloretin and 4,4'-dihydroxychalcon represented by the following Formulas (d) to (n), which are isolated from *Anemarrhena asphodeloides* Bunge, as an active ingredient.

[Formula 4]

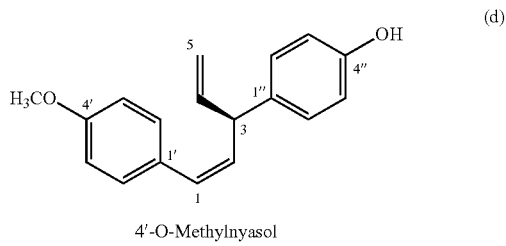

4'-O-Methylnyasol

[Formula 5]

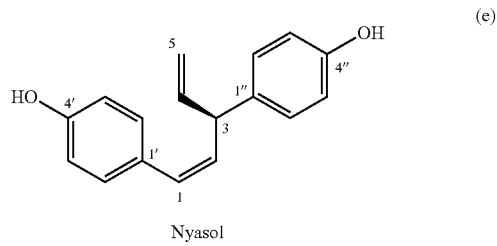

Nyasol

[Formula 6]

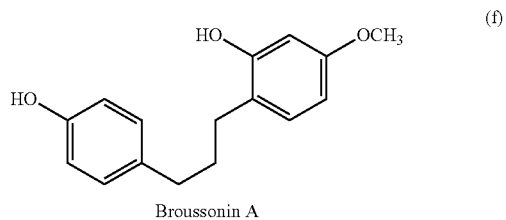

Broussonin A

[Formula 7]

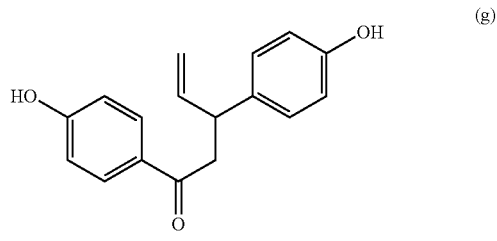

1,3-bis-di-p-hydroxyphenyl-4-penten-1-one

[Formula 8]

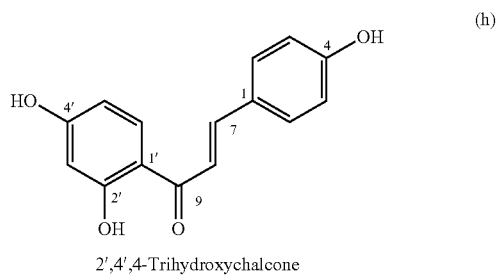

2',4',4-Trihydroxychalcone

[Formula 9]

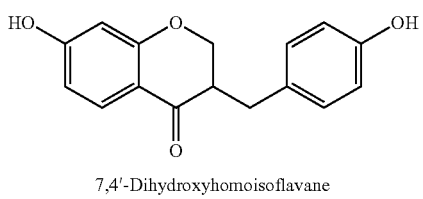

7,4'-Dihydroxyhomoisoflavane

[Formula 10]

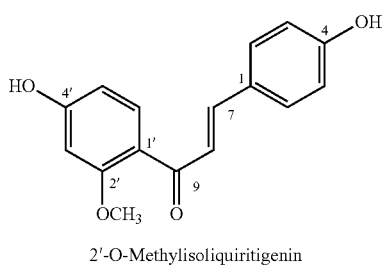

2'-O-Methylisoliquiritigenin

[Formula 11]

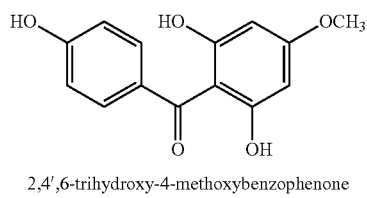

2,4',6-trihydroxy-4-methoxybenzophenone

[Formula 12]

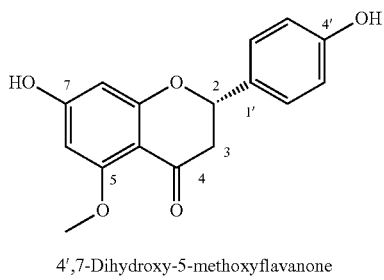

4',7-Dihydroxy-5-methoxyflavanone

[Formula 13]

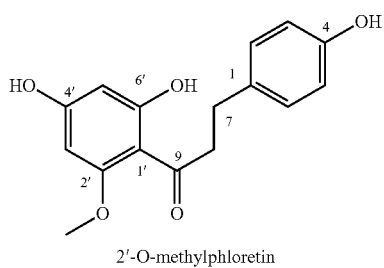

2'-O-methylphloretin

[Formula 14]

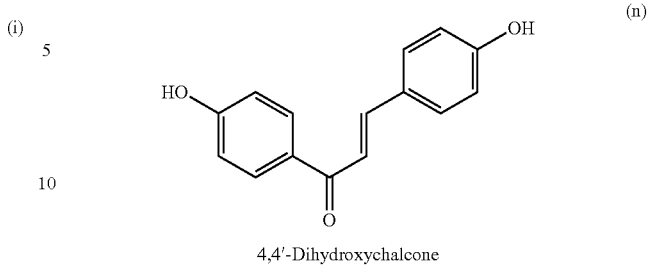

4,4'-Dihydroxychalcone

The lipid metabolism disorders include obesity, diabetes, hypercholesterolemia, hyperlipidemia, dyslipidemia, lipoproteinemia, and arteriosclerosis, and preferably obesity or diabetes.

Hereinafter, the present invention will be described in detail.

*Anemarrhena asphodeloides* Bunge powder is mixed with approximately 1 to 40-fold, preferably, 1 to 10-fold volume of water, C1 to C4 lower alcohol, or the mixtures thereof, preferably water or methanol, extracting them at room temperature (from 20 to 100° C., preferably from 20 to 30° C.) for the period ranging from about 1 hour to 10 days, preferably about 20 to 30 hours by cold water extraction, hot water extraction, ultrasonic extraction or reflux extraction, preferably reflux extraction, and repeating the extraction 1 to 10 times, preferably 2 to 7 times, and then followed by concentration under reduced pressure to obtain the crude extract.

The compounds of the present invention were prepared by the following method: Step 1 is cutting the dried *Anemarrhena asphodeloides* Bunge into small pieces, mixing the pieces with approximately 1 to 20-fold, preferably, 1 to 10-fold volume of water, $C_1$ to $C_4$ lower alcohol, or the mixtures thereof, preferably water or methanol, extracting them at room temperature (from 20 to 100° C., preferably from 20 to 30° C.) for the period ranging from about 1 hour to 10 days, preferably about 20 to 30 hours by cold water extraction, hot water extraction, ultrasonic extraction or reflux extraction, preferably reflux extraction, and repeating the extraction 1 to 10 times, preferably 2 to 7 times, and then followed by concentration under reduced pressure to obtain the crude extract; Step 2 is suspending the crude extract in water, and extracting it with ethyl acetate and water; Step 3 is performing silica gel column chromatography of the ethyl acetate extract obtained in Step 2 using an elution solvent of n-hexane:ethyl acetate (1~50:1 (v/v)) to obtain 25 fractions; Step 4 is further performing silica gel column chromatography of one fraction of the fractions obtained in Step 3 using a solvent mixture of chloroform:methanol (1~100:1 (v/v)) to obtain several fractions; and then performing silica gel column chromatography or Semiprep. HPLC of the fractions of Step 4 to obtain the novel compounds 1 to 3 of the present invention and the known compounds 4 to 14.

The composition for the prevention and treatment of lipid metabolism disorders of the present invention comprises the extract *Anemarrhena asphodeloides* Bunge or the compounds in an amount of 0.1 to 50% by weight, based on the total weight of the composition.

However, the composition is not limited thereto, and varies depending on the patient's condition and type and severity of disease The composition of the present invention may further comprise suitable carriers, excipients and diluents typically used for the preparation of pharmaceutical compositions.

According to conventional methods, the composition according to the present invention may be formulated into an oral preparation such as a powder, a granule, a tablet, a capsule, a suspension, an emulsion, a syrup, and an aerosol, an external preparation, suppository, or a sterilized injectable solution. Examples of the carriers, excipients, and diluents contained in the composition comprising the compound of the present invention may include lactose, dextrose, sucrose, sorbitol, mannitol, xylitol, erythritol, maltitol, starches, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil. Such preparations may be prepared using diluents or excipients ordinarily employed, such as a filler, an extender, a binder, a wetting agent, a disintegrating agent, and a surfactant. Examples of the solid preparation for oral administration include a tablet, a pill, a powder, a granule, and a capsule, and the solid preparation may be prepared by mixing the compound with at least one excipient such as starch, calcium carbonate, sucrose, lactose, and gelatin. Such preparations may be prepared using diluents or excipients ordinarily employed, such as a filler, an extender, a binder, a wetting agent, a disintegrating agent, and a surfactant. Examples of the solid preparation for oral administration include a tablet, a pill, a powder, a granule, and a capsule, and the solid preparation may be prepared by mixing the extract or fraction with at least one excipient such as starch, calcium carbonate, sucrose, lactose, and gelatin. Further, in addition to the excipients, lubricants such as magnesium stearate and talc may be used. Examples of a liquid preparation for oral administration include a suspension, a liquid for internal use, an emulsion, and a syrup, and various excipients such as a wetting agent, a sweetener, a flavor, and a preservative may be contained, in addition to general diluents such as water and liquid paraffin. Examples of the preparation for parenteral administration include an aseptic aqueous solution, a non-aqueous solvent, a suspension, an emulsion, a lyophilized agent, and suppository. As the non-aqueous solvent and suspension, propylene glycol, polyethylene glycol, plant oil such as olive oil, injectable ester such as ethyloleate may be used. As a suppository base, witepsol, macrogol, tween 61, cacao butter, lauric butter, glycerogelatin or the like may be used.

An effective dosage of the present compound may be determined depending on the patient's condition and body weight, severity of the diseases, drug formulation, administration routes, and administration time, and may be suitably selected by those skilled in the art. However, for better efficacy, the compound of the present invention may be administered at a daily dosage of 0.01 mg/kg to 10 g/kg, preferably 1 mg/kg to 1 g/kg once or several times. However, the scope of the present invention is not limited to any particular dosage.

The composition of present invention may be administered to mammals such as rat, mouse, domestic animals and human via various routes. All modes of administration are contemplated, for example, administration can be made orally, rectally or by intravenous, intramuscular, subcutaneous, epidural or intracerebroventricular injection.

*Further, the present invention provides a functional food for the prevention and improvement of lipid metabolism disorders, comprising the extract of *Anemarrhena asphodeloides* Bunge, as an active ingredient.

Further, the present invention provides a functional food for the prevention and improvement of lipid metabolism disorders, comprising the novel compound represented by Formula (a), (b) or (c), or the pharmaceutically acceptable salt thereof, which is isolated from *Anemarrhena asphodeloides* Bunge, as an active ingredient.

The present invention provides a functional food for the prevention and improvement of lipid metabolism disorders, comprising a compound selected from 4'-O-methylnyasol, Nyasol, Broussonin A, 1,3-bis-di-p-hydroxyphenyl-4-penten-1-one, 2',4',4-trihydroxychalcone, 7,4'-dihydroxyhomoisoflavane, 2'-O-methylisoliquiritigenin, 2,4',6-trihydroxy-4-methoxybenzophenone, 4',7-dihydroxy-5-methoxyflavanone, 2'-O-methylphloretin and 4,4'-dihydroxychalcon represented by the Formulas (d) to (n), which are isolated from *Anemarrhena asphodeloides* Bunge, as an active ingredient.

The composition of the present invention may be used in various drugs, foods, and drinks for the prevention and improvement of lipid metabolism disorders. Examples of addable food comprising the extract of *Anemarrhena asphodeloides* Bunge or the compound of the present invention include various food, beverage, gum, tea, vitamin complex, health improving food, and can be used as powder, granule, tablet, capsule or beverage etc.

Since the compound of the present invention does not have any toxicity and side effects, it is possible to use it for a long time for the purpose of prevention.

For the purpose of preventing and improving lipid metabolism disorders, the extract of *Anemarrhena asphodeloides* Bunge or the compounds of the present invention may be added to food or beverage, wherein the amount of the extract or above compound in food or beverage may generally range from about 0.01 to 15% by weight, based on the total weight of the functional health food composition, and 0.02 to 10 g, preferably 0.3 to 1 g, based on 100 ml of the health beverage composition.

Providing that the health beverage composition of present invention contains the above described compound as an essential component in the indicated ratio, there is no particular limitation on the other liquid component, wherein the other component can be various flavors or natural carbohydrates etc., like a conventional beverage. Examples of the aforementioned natural carbohydrates include monosaccharide such as glucose and fructose; disaccharide such as maltose and sucrose; conventional sugar such as dextrin and cyclodextrin; and sugar alcohol such as xylitol, sorbitol and erythritol. As another deodorant than the aforementioned ones, a natural deodorant (taumatin, stevia extract such as levaudioside A, glycyrrhizin, etc.) and synthetic deodorant (saccharin, aspartame, etc.) may be useful favorably. The amount of the above described natural carbohydrate generally ranges from about 1 to 20 g, preferably 5 to 12 g, based on 100 ml of present composition.

The components other than the aforementioned composition are various nutrients, vitamins, minerals or electrolytes, synthetic and natural flavoring agents, coloring agents and improving agents (in the case of cheese, chocolate, etc.), pectic acid and the salt thereof, alginic acid and the salt thereof, organic acid, protective colloidal adhesive, a pH controlling agent, a stabilizer, a preservative, glycerin, alcohol, or carbonizing agent used in carbonate beverage. The component other than the aforementioned ones may be fruit juice for preparing natural fruit juice, fruit juice beverage and vegetable beverage, wherein the component can be used independently or in combination. The composition ratio of the components is not so important but generally ranges from about 0 to 20 parts by weight per 100 parts by weight of the present composition.

MODE FOR THE INVENTION

Hereinafter, the present invention will be described in detail with reference to Examples and Experimental Examples.

However, these Examples and Experimental Example are provided only for the purpose of illustrating the present invention, and accordingly it is not intended that the present invention is limited thereto.

EXAMPLE 1

Preparation of Crude Extract of *Anemarrhena asphodeloides* Bunge

1-1. Preparation of Methanol Extract 20 kg of *Anemarrhena asphodeloides* Bunge purchased from omniherb.com (www.omniherb.com) was put in 20 L of 100% methanol, and extracted in a water bath using a reflux cooling device for 24 hrs. This procedure was repeated more than five times, and the supernatant was collected, and concentrated under reduced pressure to obtain 4000 g of the crude extract of *Anemarrhena asphodeloides* Bunge.

1-2. Preparation of Ethanol Extract 20 kg of *Anemarrhena asphodeloides* Bunge purchased from omniherb.com (www.omniherb.com) was put in 200 L of 90% ethanol, and extracted in a water bath using a reflux cooling device for 24 hrs. This procedure was repeated more than five times, and the supernatant was collected, and concentrated under reduced pressure to obtain 4000 g of the crude extract of *Anemarrhena asphodeloides* Bunge.

EXAMPLE 2

Preparation of Polar and Non-Polar Solvent Factions of *Anemarrhena asphodeloides* Bunge 400 g of the crude extract of *Anemarrhena asphodeloides* Bunge obtained in Example 1-1 was suspended in 4 L of distilled water, and then dissolved in 1 L of hexane to isolate the hexane-soluble components only, which were dried under vacuum. This procedure was repeated 10 times to obtain 100 g of hexane fraction. 4 L of ethyl acetate was added to the remaining aqueous layer, and the ethyl acetatesoluble components were isolated and dried under vacuum. This procedure was repeated 10 times to obtain 90 g of ethyl acetate fraction. 210 g of n-butanol fraction and 4000 g of aqueous layer were obtained by repeating the same procedure.

EXAMPLE 3

Compounds Isolated from *Anemarrhena asphodeloides* Bunge

The following compounds were examined using an analytical TLC to evaluate the purity of each component. Once the compounds were identified as single active components, their structure was determined by different types of spectroscopy, including IR (Bio-Rad Laboratories, USA), Mass (JOEL, Japan), $^1$H-NMR (Varian, Calif.), $^{13}$C-NMR, DEPT, HSQC, HMBC, COSY, NOESY, polarimeter (Jasco P-1010), and CD (Jasco J-810).

3-1. Isolation and Purification of (−)-4'-O-methylnyasol

Among the solvent fractions obtained in Example 2, the most active ethyl acetate fraction of 75 g was subjected to silica gel column chromatography (Ø15×70 cm, Merk) using a gradient solvent system of hexane:ethyl acetate (50:1→1:1 v/v) to afford 25 fractions (F1~F25). Among these fractions, Fraction 8 (F8) of 10 g was subjected to silica gel column chromatography (Ø8×70 cm, Merk) using a gradient solvent system of chloroform:methanol (100:1→10:1) to afford 5 subfractions (F8-1~F8-5). Among these fractions, Fraction 3 (F8-3) of 10 g was subjected to silica gel column chromatography (Ø5×60 cm, Merk) using a gradient solvent system of chloroform:methanol (100:1→10:1) to afford 5 subfractions (F8-3-1~F8-3-5). Subsequently, Subfraction (F8-3-2) was subjected to Semiprep. HPLC (YMC-pack ODS-A, Ø2×30 cm, methanol:water (75:25 v/v)) to yield the known compound 4 (15 mg) represented by the following Formula (4) (Preparative isolation and purification of four compounds from the Chinese medicinal herb rhizoma Anemarrhenae by high-speed counter-current chromatography, *Journal of chromatography*, 1104, pp. 69-74, A 2006).

Compound (4): (−)-4'-O-Methylnyasol

Colorless gum;
$C_{18}H_{18}O_2$.
$[\alpha]^{20}{}_D = -65.7°$ (c=0.75, MeOH). CD (MeOH, c=0.15× $10^{-2}$M): $[\theta]_{228}$+12.5, $[\theta]_{252}$−52.9;
EI-MS: m/z (%)=266;
$^1$H-NMR (400 MHz, CDCl$_3$) δ: 7.24 (2H, d, J=8.4 Hz, H-2', 6'), 7.12 (2H, d, J=8.4 Hz, H-2", 6"), 6.87 (2H, d, J=8.8 Hz, H-3', 5'), 6.78 (2H, d, J=8.8 Hz, H-3", 5"), 6.54 (1H, d, J=11.6 Hz, H-1), 6.05 (1H, m, H-4), 5.70 (1H, t, J=11.4, 10.6 Hz, H-2), 5.14 5.19 (2H, m, H-5), 4.52 (1H, t, J=9.6, 6.0 Hz, H-3), 3.80 (3H, s, OCH$_3$);
$^{13}$C-NMR (100 MHz, CDCl$_3$) δ: 158.7 (s, C-4'), 154.2 (s, C-4"), 140.9 (d, C-4), 135.8 (s, C-1"), 131.9 (d, C-2), 130.0 (s, C-1'), 129.9 (d, C-2', 6'), 129.1 (d, C-2", 6"), 128.8 (d, C-1), 115.6 (d, C-3", 5"), 115.2 (t, C-5), 113.9 (d, C-3', 5'), 55.4 (q, OCH$_3$), 47.0 (d, C-3).

3-2. Isolation and Purification of (−)-Nyasol and Broussonin A

Among the solvent fractions obtained in Example 2, the most active ethyl acetate fraction of 75 g was subjected to silica gel column chromatography (Ø15×70 cm, Merk) using a gradient solvent system of hexane:ethyl acetate (50:1→1:1 v/v) to afford 25 fractions (F1~F25). Among these fractions, Fraction 8 (F8) of 10 g was subjected to silica gel column chromatography (Ø8×70 cm, Merk) using a gradient solvent system of chloroform:methanol (100:1→10:1) to afford 5 subfractions (F8-1~F8-5). Among these fractions, Fraction 3 (F8-3) of 10 g was subjected to silica gel column chromatography (Ø5×60 cm, Merk) using a gradient solvent system of chloroform:methanol (100:1→10:1) to afford 5 subfractions (F8-3-1~F8-3-5). Subsequently, Subfraction (F8-3-3) was subjected to silica gel column chromatography (Ø8×70 cm, Merk) using a gradient solvent system of hexane:ethyl acetate (50:1→10:1 v/v) to yield each of the known compounds 5 (2.0 g) and 6 (10 mg) represented by the following Formula (5) to (6) (Minami E., et al., Stereochemistry of cis- and trans-hinokiresinol and their estrogen-like activity, *Chemical & pharmaceutical bulletin*, 48, pp. 389-392, 2000; Takasugi M., et al., Studies on phytoalexins of the Moraceae. 5.

Broussonins A and B, new phytoalexins from diseased paper mulberry, *Chemistry Letters* 3, pp. 339-340, 1980).

Compound (5): (−)-Nyasol

Yellow sticky oil
$C_{17}H_{16}O_2$. $[\alpha]^{20}_D = -75.3°$ (c 0.5, MeOH)
$IR_{max}$ 3369, 1609, 1511, 1460, 1033, 918 $cm^{-1}$
$UV_{max}$ (log ε)) 207 nm (4.47), 257 nm (4.09)
$^1$H-NMR (400 MHz, CDCl$_3$) δ: 7.18 (2H, d, J=8.4 Hz, H-2' and H-6'), 7.11 (2H, d, J=8.8 Hz, H-2" and H-6"), 6.80 (2H, d, J=8.8 Hz, H-3' and H-5'), 6.78 (1H, d, J=8.4 Hz, H-3" and H-5"), 6.53 (1H, d, J=11.2 Hz, H-1), 6.05 (1H, ddd, J=16.8, 11.2, 6.4 Hz, H-4), 5.70 (1H, t, J=11.6, 10 Hz, H-2), 5.13-5.18 (2H, m, H-5), 4.51 (1H, dd, J=6, 10 Hz, H-3);
$^{13}$C NMR (100 MHz, CDCl$_3$) δ: 128.8 (C-1), 131.9 (C-2), 47.0 (C-3), 140.9 (C-4), 115.2 (C-5), 130.1 (C-1'), 130.2 (C-2' and 6'), 115.3 (C-3' and 5'), 154.7 (C-4'), 135.8 (C-1"), 129.1 (C-2" and 6"), 115.6 (C-3" and 5"), 154.2 (C-4")
LREIMS m/z (% rel. int.) 252 ([M]$^+$, 100), 237 (25), 158 (54), 145 (50), 131 (22), 107 (58).

Compound (6): Broussonin A (Broussonin A)

Amorphous solid.
$IR_{max}$ 3400, 1615, 1590, 1515 $cm^{-1}$
$UV_{max}$ (log ε) 287.0 nm (3.63), 280.0 nm (3.69), and 225 nm (4.23);
$^1$H-NMR (400 MHz, CD$_3$OD) δ: 6.96 (2H, d, J=8.8 Hz, H-2" and 6"), 6.86 (1H, d, J=8.0 Hz, H-6'), 6.70 (2H, d, J=8.4 Hz, H-3" and 5"), 6.38 (1H, d, J=2.0 Hz, H-3'), 6.31 (1H, dd, J=7.6, 2.0 Hz, H-5'), 3.72 (3H, OCH$_3$), 2.50 (2H, t, J=7.6 Hz, H-1), 2.49 (2H, t, J=7.2 Hz, H-3), 1.79 (2H, m, H-2).
$^{13}$C NMR (100 MHz, CD$_3$OD) δ: 159.8 (s, C-4'), 157.7 (s, C-2"), 156.2 (s, C-4"), 135.0 (s, C-1"), 131.2 (d, C-6'), 130.4 (d, C-2" and 6"), 122.9 (s, C-1'), 116.1 (d, C-3" and 5"), 107.6 (d, C-5"), 99.8 (d, C-3'), 55.7 (q, OCH$_3$), 35.9 (C-3), 33.6 (C-2), 30.3 (C-1); LREIMS m/z (% rel. int.) 258 ([M]$^+$, 100), 151 (22), 137 (100), 134 (21), 107 (35), 91 (4), 77 (10).

3-3. Isolation and Purification of (E)-4'-demethyl-6-methyleucomin ((E)-5,7-dihydroxy-3-(4'-hydroxy-benzylidene)-6-methylchroman-4-one), 1,3-bis-di-p-hydroxyphenyl-4-penten-1-one, 2',4',4-trihydroxychalcone, and 7,4'-Dihydroxyhomoisoflavane Among the solvent fractions obtained in Example 2, the most active ethyl acetate fraction of 75 g was subjected to silica gel column chromatography (Ø15×70 cm, Merk) using a gradient solvent system of hexane:ethyl acetate (50:1→1:1 v/v) to afford 25 fractions (F1~F25). Among these fractions, Fraction 11 (F11) of 3 g was subjected to silica gel column chromatography (Ø8×70 cm, Merk) using a gradient solvent system of chloroform:methanol (50:1→5:1) to afford 16 subfractions (F11-1~F11-16). Among these fractions, Fraction 16 (F11-16) was subjected to Semiprep. HPLC(YMC-pack ODS-A, Ø2×30 cm, methanol:water (75:25 v/v)) to yield a novel compound 1 (5 mg) represented by the following Formula (1) and the known compounds 7 (8 mg), 8 (10 mg) and 9 (2 mg) represented by the following Formula (7) to (9) (Jeong S J., et al., Norlignans with Hyaluronidase Inhibitory Activity From *Anemarrhena asphodeloides* Planta Med, 65, pp. 367-368, 1999; Abd El-Hafiz M A., et al., Minor phenolic constituents of Crinum augustum, *Journal of Natural Products*, 53, pp. 1349-1352, 1990; Camarda L., et al., Dragon's blood from Dracaena draco, structure of novel homoisoflavonoids, *Hetero cycles*, 20, pp. 39-43, 1983).

Compound (1): (E)-5,7-Dihydroxy-3-(4'-hydroxy-benzylidene)-6-methylchroman-4-one (hereinbelow, referred as (E)-4'-demethyl-6-methyleucomin)

Yellow powder.
IR $v_{max}$ (KBr) 3368, 2913, 1730, 1595, 1467 $cm^{-1}$;
$UV_{max}$ (log) (MeOH) 288 (3.8) nm;
$^1$H-NMR (400 MHz, CD$_3$OD) δ: 5.27 (2H, d, J=1.6 Hz, H-2), 5.88 (1H, s, H-8), 6.87 (2H, dd, J=2.0, 8.4 Hz, H-3',5'), 7.23 (2H, dd, J=2.0, 8.4 Hz, H-2', 6'), 7.72 (1H, s, H-7'), 1.95 (3H, s, 6-CH$_3$);
$^{13}$C-NMR (100 MHz, CD$_3$OD) δ68.6 (C-2), 128.9 (C-3), 186.6 (C-4), 103.4 (C-4a), 163.5 (C-5), 105.7 (C-6), 166.3 (C-7), 95.1 (C-8), 161.6 (C-8a), 127.2 (C-1'), 133.6 (C-2', 6'), 116.9 (C-3', 5'), 160.7 (C-4'), 137.9 (C-7'), 7.1 (6-CH$_3$);
HRFABMS m/z 299.0922 [M+H]$^+$ (calcd for $C_{17}H_{14}O_5$, 299.0919).

Compound (7):
1,3-bis-di-p-hydroxyphenyl-4-penten-1-one

Amorphous solid.
$C_{17}H_{16}O_3$.
$IR_{max}$ 3370, 1653, 1511, 1460 $cm^{-1}$;
$UV_{max}$ (log ε) 265 nm (4.09);
$^1$H-NMR (400 MHz, CD$_3$OD) δ: 7.85 (2H, d, J=8.4 Hz, H-2" and H-6"), 7.11 (2H, d, J=8.8 Hz, H-2' and H-6'), 6.89 (2H, d, J=8.4 Hz, H-3" and H-5"), 6.74 (2H, d, J=8.8 Hz, H-3' and H-5'), 6.03 (1H, m, H-4), 4.95 (2H, m, H-5), 4.00 (1H, q, J=7.2 Hz, H-3), 3.32 (2H, dd, J=3.2, 7.2 Hz, H-2);
$^{13}$C-NMR (100 MHz, CD$_3$OD) δ: 196.0 (C-1), 44.2 (C-2), 45.1 (C-3), 143.1 (C-4), 113.9 (C-5), 135.2 (C-1'), 139.7 (C-2' and 6'), 116.0 (C-3' and 5'), 156.7 (C-4'), 130.6 (C-1"), 131.4 (C-2" and 6"), 116.0 (C-3" and 5"), 162.6 (C-4");
EIMS m/z: 268 [M]$^+$.

Compound (8): 2',4',4-Trihydroxychalcone

Yellow powder.
$C_{15}H_{12}O_4$.
$^1$H-NMR (400 MHz, CDCl$_3$) δ: 6.28 (1H, d, J=2.4 Hz, H-3'), 6.41 (1H, dd, J=2.8, 8.8 Hz, H-5'), 6.83 (2H, d, J=8.4 Hz, H-2, 6), 7.59 (1H, d, J=15.9 Hz, H-8), 7.62 (2H, d, J=8.4 Hz, H-3, 5), 7.77 (1H, d, J=15.9 Hz, H-7), 7.96 (1H, d, J=15.9 Hz, H-6');
$^{13}$C NMR (100 MHz, CDCl$_3$) δ: 127.9 (C-1), 131.8 (C-2, 6), 116.9 (C-3, 5), 161.6 (C-4), 145.7 (C-7), 118.4 (C-8), 193.5 (C-9), 114.7 (C-1'), 167.5 (C-2'), 103.8 (C-3'), 166.4 (C-4'), 109.2 (C-5'), 133.4 (C-6').
EIMS m/z: 256 [M]$^+$.

Compound (9): 7,4'-Dihydroxyhomoisoflavane

Yellow powder.
$C_{16}H_{14}O_4$.
UV (MeOH) max (log) 288 (4.03) nm;
IR (KBr) 3350 (br), 1670, 1610, 1520, 1022, 930 $cm^{-1}$;
EI-MS: m/z (%)=270 [M]$^+$.
$^1$H-NMR (400 MHz, CD$_3$OD) δ 2.6, 3.0 (2H, m, H-7'), 2.7 (1H, m, H-3), 4.0 (2H, m, H-2), 6.2 (1H, d, J=2.0 Hz, H-8), 6.4 (1H, d, J=2.0, 8.8 Hz, H-6), 6.70 (2H, d, J=8.4 Hz, H-3', 5'), 7.0 (2H, d, J=8.4 Hz, H-2', 6'), 7.7 (1H, dd, J=8.8 Hz, H-5);
$^{13}$C-NMR (100 MHz, CD$_3$OD) δ 70.0 (C-2), 49.0 (C-3), 195.2 (C-4), 130.4 (C-5), 111.2 (C-6), 166.5 (C-7), 103.3

(C-8), 114.6 (C-4a), 165.0 (C-8a), 130.5 (C-1'), 131.4 (C-2'/C-6'), 116.2 (C-3'/C-5'), 157.9 (C-4').

3-4. Isolation and Purification of 2'-O-methylisoliquiritigenin (8 mg) and 2,4',6-trihydroxy-4-methoxybenzophenone Among the solvent fractions obtained in Example 2, the most active ethyl acetate fraction of 75 g was subjected to silica gel column chromatography (Ø15×70 cm, Merk) using a gradient solvent system of hexane:ethyl acetate (50:1→1:1 v/v) to afford 25 fractions (F1~F25). Among these fractions, Fraction 11 (F11) of 3 g was subjected to silica gel column chromatography (Ø8×70 cm, Merk) using a gradient solvent system of chloroform:methanol (50:1→5:1) to afford 16 sub-fractions (F11-1~F11-16). Among these fractions, Fraction 14 (F11-14) was recrystallized using a mixed solvent of methanol:chloroform (1:1) to yield the known compounds 10 (8 mg) and 11 (1.5 g) represented by the following Formula (10) to (11) (Namikoshi M., et al., Homoisoflavonoids and related compounds. III. Phenolic constituents of *Caesalpinia japonica* Sieb. et Zucc., *Chemical & Pharmaceutical Bulletin*, 35, pp. 3568-3575, 1987; Matsuda H., et al., Testosterone 5-reductase inhibitory active constituents from *Anemarrhenaerhizoma*, *Biological & Pharmaceutical Bulletin*, 24, pp. 586-587, 2001).

Compound (10): 2'-O-Methylisoliquiritigenin

Yellow powder.
$C_{16}H_{14}O_4$.
UV (MeOH) max (log) 286 (3.88) nm;
IR (KBr) 3360 (br), 1675, 1620, 1510, 930 cm$^{-1}$;
EI-MS: m/z (%)=270 [M]$^+$.
$^1$H-NMR (400 MHz, CD$_3$OD) δ 6.44 (1H, dd, J=8.4, 2.0 Hz, H-5'), 6.51 (1H, d, J=2.0 Hz, H-3'), 6.81 (2H, d, J=8.8 Hz, H-3, 5), 7.38 (1H, d, J=15.6 Hz, H-8), 7.50 (2H, d, J=8.4 Hz, H-3), 7.53 (1H, d, J=15.6 Hz, H-7), 7.56 (1H, d, J=2.0 Hz, H-3');
$^{13}$C-NMR (100 MHz, CD$_3$OD) δ 128.0 (C-1), 131.5 (C-2, 6), 117.0 (C-3, 5), 161.3 (C-4), 144.2 (C-7), 125.2 (C-8), 193.0 (C-9), 121.9 (C-1'), 162.6 (C-2'), 100.0 (C-3'), 164.6 (C-4'), 109.0 (C-5'), 133.8 (C-6').

Compound (11): 2,4',6-trihydroxy-4-methoxybenzophenone

Yellow powder.
$C_{14}H_{12}O_5$.
IR$_{max}$ (KBr) 3177, 1661, 1249, 831 cm$^{-1}$;
UV$_{max}$ (log ε) (MeOH) 298 (4.3) nm;
$^1$H-NMR (400 MHz, CD$_3$OD) δ: 5.97 (2H, s, H-3, 5), 6.76 (2H, d, J=8.9 Hz, H-3', 5'), 7.61 (2H, d, J=8.9 Hz, H-2', 6'), 3.77 (3H, s, OCH$_3$);
$^{13}$C-NMR (100 MHz, CD$_3$OD) δ: 108.1 (C-1), 162.5 (C-2, 6), 94.5 (C-3, 5), 166.1 (C-4), 197.8 (C=O), 133.1 (C-1'), 115.2 (C-2', 6'), 132.4 (C-3', 5'), 162.0 (C-4'), 55.9 (OCH$_3$);
EIMS m/z 260 [M]$^+$.

3-5. Isolation and Purification of Anemarcoumarin A, 4',7-dihydroxy-5-methoxyflavanone, and 2'-O-methylphloretin Among the solvent fractions obtained in Example 2, the most active ethyl acetate fraction of 75 g was subjected to silica gel column chromatography (Ø15×70 cm, Merk) using a gradient solvent system of hexane:ethyl acetate (50:1→1:1 v/v) to afford 25 fractions (F1~F25). Among these fractions, Fraction 22 (F22) of 5 g was subjected to silica gel column chromatography (Ø10×70 cm, Merk) using a gradient solvent system of chloroform:methanol (50:1→5:1). Fraction 5 (F22.5) was subjected to Semiprep. HPLC(YMC-pack ODS-A, Ø2×30 cm, methanol:water (60:40 v/v)) to yield a novel compound 2 (2 mg) represented by the following Formula (2) and the known compounds 12 (5 mg) and 13 (10 mg) represented by the following Formulas (12) to (13) (Herath W., et al., Identification and biological activity of microbial metabolites of xanthohumol, *Chemical & Pharmaceutical Bulletin*, 51, pp. 1237-1240, 2003; Barrero A F., et al., Resorcinol Derivatives and Flavonoids of Ononis natrix subspecies ramosissima, *Journal of Natural Products*, 60, pp. 6568, 1997).

Compound (2): 7-Hydroxy-3-(4-hydroxybenzyl)coumarin (hereinbelow, referred as Anemarcoumarin A)

*Yellow powder.
IR ν$_{max}$ (KBr) 3298, 2918, 1690, 1610, 1454 cm$^{-1}$;
UV$_{max}$ (log) (MeOH) 286 (4.2) nm;
$^1$H-NMR (400 MHz, CD$_3$OD) δ: 3.6 (2H, s, H-7'), 6.68 (1H, d, J=2.0 Hz, H-8), 6.73 (2H, d, J=8.8 Hz, H-3', 5'), 6.75 (1H, dd, J=2.0, 8.4 Hz, H-6), 7.10 (2H, d, J=8.8 Hz, H-2', 6'), 7.32 (1H, d, J=8.4 Hz, H-5), 7.45 (1H, s, H-3);
$^{13}$C-NMR (100 MHz, CD$_3$OD) δ164.3 (C-2), 126.2 (C-3), 141.7 (C-4), 113.8 (C-4a), 130.1 (C-5), 114.5 (C-6), 162.3 (C-7), 103.1 (C-8), 156.2 (C-8a), 130.6 (C-1'), 131.3 (C-2', 6'), 116.5 (C-3', 5'), 157.3 (C-4'), 36.5 (C-7');
HREIMS m/z 268.0738 [M]$^+$ (calcd for $C_{16}H_{12}O_4$, 268.0735).

Compound (12): 4',7-Dihydroxy-5-methoxyflavanone

Yellow powder.
$C_{16}H_{14}O_5$.
EI-MS: m/z (%)=286;
IR ν$_{max}$ (KBr) 3300, 1670, 1620, 1510 cm$^{-1}$;
UV$_{max}$ (log) (MeOH) 260 (4.0) nm;
$^1$H-NMR (400 MHz, CDCl$_3$) δ 3.10 (2H, m, H-3), 5.31 (1H, dd, J=2.8, 12.8 Hz, H-2), 5.94 (1H, d, J=2.4 Hz, H-8), 6.04 (1H, d, J=2.4 Hz, H-6), 6.76 (2H, d, J=8.4 Hz, H-3',5'), 7.27 (2H, d, J=8.4 Hz, H-2'/H-6'), 3.73 (3H, OMe-5);
$^{13}$C-NMR (100 MHz, CDCl$_3$) δ 78.0 (C-2), 44.7 (C-3), 187.7 (C-4), 162.1 (C-5), 93.1 (C-6), 164.2 (C-7), 95.5 (C-8), 104.0 (C-4a), 164.2 (C-8a), 129.3 (C-1'), 128.0 (C-2'/C-6'), 115.0 (C-3'/C-5'), 157.5 (C-4'), 55.7 (OMe).

Compound (13): 2'-O-methylphloretin

Yellow powder.
$C_{16}H_{16}O_5$.
UV (MeOH) max (log) 288 (3.98) nm;
IR (KBr) 3400 (br), 1670, 1620, 1510, 930 cm$^{-1}$;
EI-MS: m/z (%)=288 [M]$^+$.
$^1$H-NMR (400 MHz, CD$_3$OD) δ 5.88 (1H, dd, J=8.4, 2.0 Hz, H-5'), 5.95 (1H, d, J=2.0 Hz, H-3'), 6.68 (2H, d, J=8.8 Hz, H-3/5), 7.02 (2H, d, J=8.8 Hz, H-2/6), 2.83, 3.15 (2H, m, H-7), 3.2 (2H, m, H-8);
$^{13}$C-NMR (100 MHz, CD$_3$OD) δ 133.9 (C-1), 130.4 (C-2, 6), 116.3 (C-3, 5), 156.6 (C-4), 31.5 (C-7), 47.5 (C-8), 206.1 (C-9), 106.1 (C-1'), 165.0 (C-2'), 92.2 (C-3'), 168.4 (C-4'), 97.1 (C-5'), 166.6 (C-6').

3-6. Isolation and Purification of Anemarchalconyn and 4,4'-Dihydroxychalcon Among the solvent fractions obtained in Example 2, the most active ethyl acetate fraction of 75 g was subjected to silica gel column chromatography (Ø15×70 cm, Merk) using a gradient solvent system of hexane:ethyl acetate (50:1→1:1 v/v) to afford 25 fractions (F1~F25). Among these fractions, Fraction 22 (F22) of 5 g was subjected to silica gel column chromatography (Ø10×70 cm, Merk) using a gradient solvent system of chloroform:methanol (50:1→5:1). Fraction 6 (F22.6) was subjected to Semiprep. HPLC(YMC-pack ODS-A, Ø2×30 cm, methanol:water (40:60 v/v)) to yield a novel compound 3 (2 mg) represented by the following Formula 3 and the known compound 14 (5 mg) represented by the following Formula (14) (Ohashi H., et al., 4,4'-Dihydroxychalcone from the heartwood of *Chamaecypar isobtusa*. *Phytochemistry*, 27, pp. 3993-3994, 1988).

Compound (3): 1,3-bis(4-hydroxyphenyl)prop-2-yn-1-one (hereinbelow, referred as Anemarchalconyn)

Yellow powder.
UV (MeOH) $\lambda_{max}$ (logε) 286 (4.2) nm;
IR $\nu_{max}$ (KBr) 3350, 2193, 1620, 1159 cm$^{-1}$;
$^1$H-NMR (400 MHz, CD$_3$OD) δ: 6.85 (2H, d, J=8.8 Hz, H-3", 5"), 6.90 (2H, d, J=8.8 Hz, H-3', 5'), 7.55 (2H, d, J=8.8 Hz, H-2", 6"), 8.07 (2H, d, J=8.8 Hz, H-2', 6');
$^{13}$C-NMR (100 MHz, CD$_3$OD) δ: 178.5 (C-1), 87.2 (C-2), 95.7 (C-3), 130.3 (C-1'), 133.2 (C-2', 6'), 116.6 (C-3', 5'), 165.2 (C-4'), 111.5 (C-1"), 136.3 (C-2", 6"), 117.1 (C-3", 5"), 161.8 (C-4");
HREIMS m/z 238.0630 [M]$^+$ (calcd for C$_{15}$H$_{10}$O$_3$, 238.0630).

Compound (14): 4,4'-Dihydroxychalcon

Yellow powder.
C$_{15}$H$_{12}$O$_3$.
UV (MeOH) max (log) 234, 350 (3.98) nm;
IR (KBr) 3500 (br), 1750, 1655 cm$^{-1}$;
EI-MS: m/z (%)=240 [M]$^+$.
$^1$H-NMR (400 MHz, CD$_3$OD) δ 6.83 (2H, d, J=8.4 Hz, H-3/5), 6.88 (2H, d, J=8.4 Hz, H-3'/5'), 7.55 (2H, d, J=8.4 Hz, H-2/6), 7.99 (2H, d, J=8.4 Hz, H-2'/6'), 7.61 (1H, d, J=16.0 Hz, H-7), 7.68 (1H, d, J=16.0 Hz, H-8);
$^{13}$C-NMR (100 MHz, CD$_3$OD) δ 132.4 (C-1), 129.8 (C-2, 6), 121.9 (C-3, 5), 156.6 (C-4), 125.3 (C-7), 145.0 (C-8), 190.5 (C-9), 134.2 (C-1'), 130.1 (C-2'/6'), 120.0 (C-3'/5'), 168.4 (C-4').

REFERENCE EXAMPLE 2

Preparation of 0.3% Oil-Red O Staining Solution

Oil-red O was dissolved in 100% isopropanol, and stirred for about 16 hrs to prepare a 0.3% Oil-red O staining solution. Distilled water was added to the solution at a ratio of 0.3% Oil-red O:distilled water=6:4 (v/v), and mixed with each other. The solution was filtered using 3M paper once, and filtered again using a 0.2 µm syringe filter.

EXPERIMENTAL EXAMPLE 1

Inhibitory Effect on Adipocyte Differentiation

Pre-adipocytes and 3T3-L1 cell (American Tissue Culture. Collection, ATCC) were maintained in DMEM (Dulbecco's Modified Eagle Medium, Gibco-BRL, Grand Island, N.Y., USA) supplemented with 10% bovine calf serum. 4×10$^4$ of cells were suspended in 0.5 ml and seeded in each well of 24-well plate. The cells were grown to confluence for 48 hrs in the same medium and the medium was replaced with DMEM containing insulin (5 µg/mL), 10 µM rosiglitazone, 1 µM dexamethasone, and 10% fetal bovine serum (FBS) to differentiate adipocytes. At this time, the extracts obtained in Examples 1 to 2 and the compounds obtained in Examples 3-1 to 3-6 were dissolved in DMSO, and the cells were treated with each compound at the same concentration of DMSO. As a control group, the cells were treated with Resveratrol (Sigma-Aldrich, 3,4',5-Trihydroxy-trans-stilbene, 5-[(1E)-2-(4-Hydroxyphenyl)ethenyl]-1,3-benzenediol), which is known to inhibit the adipocyte differentiation and prevent diabetes, dissolved in DMSO at the same concentration. The cells were then replaced with 10% FBS/DMEM supplemented with 5 µg/mL insulin after 48 hrs, and also re-treated with each compound. After 48 hrs, the medium was replaced with fresh 10% FBS/DMEM. Day 7 after induction of adipocyte differentiation, the differentiated adipocytes were examined by Oil-red O staining. After removing the culture medium, the cells were gently washed with PBS once, and fixed in 10% formalin at room temperature for 1 hr. After removing the formalin, the cells were washed with distilled water twice, and stained with the Oil-red O staining solution prepared in Reference Example 2 at room temperature for 1 hr. To wash off the staining solution, the cells were washed with distilled water, and dried (uncapped). After image scanning, the stained cells were treated with 100% isopropanol for 10 min to wash out the staining solution. The absorbance at 500 nm was measured to compare the Oil-red O staining between the compound-treated groups and the control group. To quantify the effect of each compound on adipocyte differentiation, the IC$_{50}$ value was determined using BioDataFit 1.02.

Consequently, as described in the following Table 1 and FIG. 1, ethylacetate extract and butanol extract showed inhibitory effects on adipocyte differentiation, indicating its excellent effects on lipid metabolism disorders.

Further, as described in the following Table 2, 4'-O-methylnyasol, 2'-O-methylisoliquiritigenin, Broussonin A, and 2',4',4-trihydroxychalcone showed inhibitory effects on adipocyte differentiation. In particular, Anemarchalconyn showed excellent inhibitory effects on adipocyte differentiation even at lower concentration than the control group Resveratrol, indicating its excellent effects on lipid metabolism disorders.

TABLE 1

|  | Inhibition(%)50 µg/ml | Inhibition(%)100 µg/ml |
| --- | --- | --- |
| Control group | 100 | 100 |
| Methanol extract | 98.2 | 70.0 |
| Hexane extract | 133.5 | 104.2 |
| Ethylacetate extract | 52.2 | 49.2 |
| Butanol extract | 97.6 | 81.6 |
| Water extract | 100.3 | 105.5 |

TABLE 2

Inhibitory Activities of Isolated Compound on Adipocyte Differentiation(IC$_{50}$)

|  | Compound | IC$_{50}$ |
| --- | --- | --- |
| Compound 1 | (E)-4'-demethyl-6-methyleucomin | 336.1 |
| Compound 2 | Anemarcoumarin A | nd |
| Compound 3 | Anemarchalconyn | 5.3 |
| Compound 4 | 4'-O-Methylnyasol | 45.9 |

TABLE 2-continued

Inhibitory Activities of Isolated Compound on Adipocyte Differentiation($IC_{50}$)

| Compound | | $IC_{50}$ |
|---|---|---|
| Compound 5 | Nyasol | 107.8 |
| Compound 6 | Broussonin A | 74.5 |
| Compound 7 | 1,3-bis-di-p-hydroxyphenyl-4-penten-1-one | 326.2 |
| Compound 8 | 2',4',4-Trihydroxychalcone | 96.4 |
| Compound 9 | 7,4'-Dihydroxyhomoisoflavane | >500 |
| Compound 10 | 2'-O-Methylisoliquiritigenin | 41.8 |
| Compound 11 | 2,4',6-trihydroxy-4-methoxybenzophenone | nd[b] |
| Compound 12 | 4',7-Dihydroxy-5-methoxyflavanone | 259.7 |
| Compound 13 | 2'-O-methylphloretin | >500 |
| Compound 14 | 4,4'-Dihydroxychalcon | >500 |
| Positive standard (Control group) | Resveratrol[a] | 31.4 |

[a] positive control
[b] not detected

Hereinafter, Preparation Examples of the pharmaceutical composition comprising the compound of the present invention will be described. However, these Preparation Examples are for illustrative purposes only, and the present invention is not intended to be limited by these Examples.

PREPARATION EXAMPLE 1

Preparation of Powder (E)-4'-demethyl-6-methyleucomin or methanol extract 20 mg
Lactose 100 mg
Talc 10 mg
The ingredients were mixed and filled in an airtight sac to prepare a powder agent.

PREPARATION EXAMPLE 2

Preparation of Tablet

Anemarcoumarin A or ethanol extract 10 mg
Corn starch 100 mg
Lactose 100 mg
Magnesium Stearate 2 mg
The ingredients were mixed and prepared into a tablet according to the conventional tabletting method.

PREPARATION EXAMPLE 3

Preparation of Capsule

Anemarchalconyn or hexane extract 10 mg
Crystalline cellulose 3 mg
Lactose 14.8 mg
Magnesium Stearate 0.2 mg
The ingredients were mixed and filled into a gelatin capsule according to a typical procedure to give a capsule agent.

PREPARATION EXAMPLE 4

Preparation of Injectable Formulation

Broussonin A or ethylacetate extract 10 mg
Mannitol 180 mg
Sterile distilled water 2974 mg
$Na_2HPO_4$ $12H_2O$ 26 mg According to a typical procedure, an injectable formulation comprising the above ingredients was prepared into a (2 ml) ampule.

PREPARATION EXAMPLE 5

Preparation of Liquid Formulation

4'-O-methylnyasol or butanol extract 20 mg
High fructose corn syrup 10 g
Mannitol 5 g
Purified water proper amount
According to a typical procedure, each ingredient was solubilized in purified water. A proper amount of lemon flavor was added to the above ingredients, and mixed. Then, purified water was added to a volume of 100 ml, filled in a brown bottle, and sterilized to prepare a liquid formulation.

PREPARATION EXAMPLE 6

Preparation of Health Beverage

2',4',4-Trihydroxychalcone 100 mg
Vitamin C 15 g
Vitamin E (powder) 100 g
Ferrous Lactate 19.75 g
Zinc oxide 3.5 g
Nicotinic acid amide 3.5 g
Vitamin A 0.2 g
Vitamin $B_1$ 0.25 g
Vitamin $B_2$ 0.3 g
Water proper amount
According to the conventional health beverage preparation method, the above components were mixed, and agitated at 85° C. for 1 hour, filtered and then filled in 2 L sterile container, followed by disinfection and sealing. Then, the health beverage of the present invention was stored in the refrigerator before use.

The composition is determined with the components proper to a relatively favorite beverage as in the preferred Examples, and the mixing ratio may be changed based on the demand class, needed countries, the purpose of use and place and national characteristic.

The invention claimed is

1. Isolated (E)-5,7-dihydroxy-3-(4'-hydroxybenzylidene)-6-methylchroman-4-one, 7-hydroxy-3-(4-hydroxybenzyl)coumarin or isolated 1,3-bis(4-hydroxyphenyl)prop-2-yn-1-one from *Anemarrhena asphodeloides* Bunge or a pharmaceutically acceptable salt thereof.

2. A method of treating lipid metabolism disorders in a human in need thereof comprising:
administering to said human in need thereof a therapeutically effective amount of isolated (E)-5,7-dihydroxy-3-(4'-hydroxybenzylidene)-6-methylchroman-4-one, 7-hydroxy-3-(4-hydroxybenzyl)coumarin or isolated 1,3-bis(4-hydroxyphenyl)prop-2-yn-1-one from *Anemarrhena asphodeloides* Bunge or a pharmaceutically acceptable salt thereof, wherein the lipid metabolism disorder is selected from the group consisting of obesity, diabetes, hypercholesterolemia, hyperlipidemia, dyslipidemia, lipoproteinemia, and arteriosclerosis.

3. A pharmaceutically acceptable salt of isolated (E)-5,7-dihydroxy-3-(4'-hydroxybenzylidene)-6-methylchroman-4-one, 7-hydroxy-3-(4-hydroxybenzyl)coumarin or isolated 1,3-bis(4-hydroxyphenyl)prop-2-yn-1-one from *Anemarrhena asphodeloides* Bunge.

* * * * *